United States Patent [19]

Anderson

[11] Patent Number: 5,039,823

[45] Date of Patent: Aug. 13, 1991

[54] METHOD FOR PREPARING INDOLENINIUM HALIDE

[75] Inventor: Bruce R. Anderson, Irwin, Pa.

[73] Assignee: PPG Industries, Inc., Pittsburgh, Pa.

[21] Appl. No.: 565,386

[22] Filed: Aug. 10, 1990

[51] Int. Cl.$^5$ ............................................ C07D 209/10
[52] U.S. Cl. ................................. 548/469; 548/480
[58] Field of Search ....................... 548/469, 480, 452

[56] References Cited

U.S. PATENT DOCUMENTS 2,016,836 10/1935 Piggot ................................. 548/469
2,559,907 7/1951 van Lare et al. .................... 548/469
2,910,515 10/1959 Luvisi et al. ......................... 548/469

Primary Examiner—David B. Springer
Attorney, Agent, or Firm—Irwin M. Stein

[57] ABSTRACT

Indoleninium halides, e.g., indoleninium iodides, are prepared by reacting the corresponding indolenine with an organic halide reactant, e.g., alkyl halide, such as methyl iodide, the organo portion of which undergoes addition to the nitrogen atom of the indolenine at conventional reaction temperatures in the presence of a high boiling (80° C.-200° C.) organic ketone solvent selected from the group consisting of acyclic ketones containing from 4 to 12 carbon atoms and alicyclic ketones containing from 4 to 10 carbon atoms.

18 Claims, No Drawings

METHOD FOR PREPARING INDOLENINIUM HALIDE

DESCRIPTION OF THE INVENTION

Spiro(indolino)-type compounds have been described as possessing photochromic properties and have been suggested for use in applications in which a color change or darkening induced by sunlight is a desirable feature. For example, spiro(indolino) naphthoxazine compounds are described in U.S. Pat. Nos. 3,562,172, 3,578,602, 4,215,010 and 4,342,668. Spiro(indolino) pyridobenzoxazines have been described in U.S. Pat. No. 4,637,698. Spiro(indolino) benzoxazines have been described in U.S. Pat. No. 4,816,584. Spiro(benzindolino)-type compounds have been described in U.S. Pat. No. 4,931,219.

The aforedescribed spiro(indolino)-type compounds are commonly prepared by reacting the corresponding indoleninium salt, e.g., the iodide salt, with an aromatic reactant, e.g., 5-nitroso (or formal)-6-hydroxy quinoline or 1-nitroso (or formal)-2-hydroxy naphthalene in the presence of a base such as triethylamine. The indoleninium salt reactant used in such condensation reaction is often not purified because of the difficulty in isolating the salt. Condensation reactions performed with the crude salt result in poor yields of the spiro(indolino)-type photochromic compound and the formation of tarry by-products. In order to avoid those adverse results, it is necessary to purify the crude indoleninium reactant or to purify the final photochromic compound, both of which can entail the expenditure of considerable cost and effort.

It has now been discovered that indoleninium salts of substantial purity may be prepared by conducting the synthesis in the presence of a high-boiling organic ketone solvent. More particularly, it has been discovered that indoleninium halides may be prepared readily in substantial purity by reaction of the corresponding indolenine reactant and an organo halide reactant, the organo portion of which undergoes addition to the nitrogen atom of the indolenine, in the presence of a solvating amount of an organic ketone selected from the group consisting of acyclic ketones containing from 4 to 12 carbon atoms and alicyclic ketones containing from 4 to 10 carbon atoms.

The indoleninium halides prepared by the aforedescribed process may be used directly to prepare spiro(indolino)-type compounds of substantial purity. Furthermore, the aforedescribed process allows the use of an impure or crude indolenine reactant since the indoleninium salt, e.g., halide, thereby prepared crystallizes readily from the reaction mixture as a substantially pure product. This benefit avoids the extra expense of purifying the crude indolenine reactant before its reaction with the organo halide.

DETAILED DESCRIPTION OF THE INVENTION

Organic ketones that may be used as a solvent in the reaction of the indolenine and organo halide reactants are relatively high-boiling organic ketones, e.g., those organic ketones that boil (at atmospheric pressure) between about 80° C. and about 200° C., e.g., between about 80° C. and about 130° C. More particularly, the organic ketones are selected from the group consisting of acyclic ketones containing from 4 to 12 carbon atoms and alicyclic ketones containing from 4 to 10 carbon atoms. Preferably, the organic ketones are those selected from the group consisting of acyclic ketones containing from 4 to 8, e.g., 4 to 6, carbon atoms and alicyclic ketones containing from 5 to 7 carbon atoms. Generally, the organic ketones will be mono-ketones, i.e., ketones having 1 carbonyl functional group; however, ketones having 2 or 3 carbonyl groups, i.e., diones or triones, are contemplated herein. Still more particularly, the preferred organic ketones are those which are readily available commercially; namely, saturated aliphatic (paraffinic) mono-ketones containing the aforedescribed number of carbon atoms.

Non-limiting examples of organic acyclic ketones meeting the above description include: butanone, 3-methyl-2-butanone, 2-pentanone, 3-pentanone, 2-methyl-3-pentanone, 3-methyl-2-pentanone, 4-methyl-2-pentanone (methyl isobutyl ketone), 3-hexanone, 2-hexanone, 2-methyl-3-hexanone, 5-methyl-2-hexanone, 2-heptanone, 3-heptanone, 4-heptanone, 2-methyl-3-heptanone, 5-methyl-3-heptanone, 2-octanone, 3-octanone, 2-nonanone, 3-nonanone, 5-nonanone, 2-decanone, 3-decanone and 4-decanone.

Non-limiting examples of alicyclic ketones meeting the aforesaid description include: cyclobutanone, cyclopentanone, 2-methylcyclopentanone, cyclohexanone, 2-methylcyclohexanone, cycloheptanone, cyclooctanone and methylcyclooctanone.

The amount of organic ketone solvent used should be sufficient to solvate the reactants and resultant product mixture, and provide a liquid medium from which the indoleninium halide product may be readily crystallized. The indoleninium halide product is soluble to a small extent in the organic ketone solvent and, therefore, a large excess of the solvent is not recommended for the reason that the greater the amount of solvent used, the more indoleninium halide product lost to the solvent. Further, a large excess of solvent requires the handling of large volumes of liquid, which is undesirable from economic and environmental considerations. The use of too little solvent results in the reaction product being a non-fluid mass, which is difficult to handle. Hence, a solvating amount, i.e., an amount which is sufficient to keep the reaction mixture and product mixture liquid and fluid, is used. Typically, the organic ketone solvent is used in amounts of from about 1 to about 5 milliliters of solvent per gram (theoretical) of indoleninium halide product. More particularly, from about 2 to about 3 milliliters of organic ketone solvent per gram of indoleninium halide product is used.

The indolenine reactant may be represented by the following graphic formula,

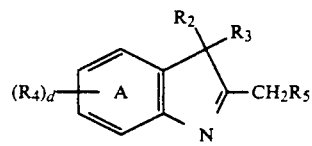

In graphic formula I, $R_2$ and $R_3$ may each be selected from the group consisting of $C_1$-$C_5$ alkyl, phenyl, mono- and di-substituted phenyl, benzyl or $R_2$ and $R_3$ may combine to form an alicyclic ring containing from 5 to 8 carbon atoms (including the spiro carbon atom). The aforesaid phenyl substituents may be selected from $C_1$-$C_4$ alkyl, e.g., methyl and ethyl, and $C_1$-$C_4$ alkoxy, e.g., methoxy, ethoxy and propoxy, radicals. More particularly, $R_2$ and $R_3$ may each be selected from $C_1$-$C_5$ alkyl, e.g., methyl, ethyl, propyl, butyl and pentyl, and phenyl. When one of $R_2$ or $R_3$ is a tertiary alkyl radical, such as tertiary butyl or tertiary amyl, the other is preferably an alkyl radical other than a tertiary alkyl radical.

In graphic formula I, each $R_4$ may be selected from $C_1$-$C_5$ alkyl, halogen, e.g., chloro, fluoro or bromo, $C_1$-$C_5$ alkoxy, nitro, cyano, $C_1$-$C_4$ monohaloalkyl, $C_1$-$C_4$ polyhaloalkyl, $C_1$-$C_8$ alkoxycarbonyl, and $C_1$-$C_4$ acyloxy, i.e., $R_cC(O)O-$, wherein $R_c$ is a $C_1$-$C_4$ alkyl, e.g., methyl. The letter "d" in graphic formula I represents an integer that may vary from 0 to 4, e.g., 0 to 2, such as 1 or 2, and denotes the number of non-hydrogen substituents. Preferably, $R_4$ is selected from the group consisting of $C_1$-$C_2$ alkyl, chloro, fluoro, $C_1$-$C_2$ trihaloalkyl, e.g., trihalomethyl such as trifluoromethyl, and $C_1$-$C_2$ alkoxy. When "d" is 0 (zero), there are no $R_4$ substituents and all of the aromatic carbon atoms have their full complement of hydrogen atoms for the indole group.

In a further embodiment, $(R_4)_d$ is a ring system, e.g., a benzene ring, fused to ring A and comprises an aromatic or heteroaromatic ring, e.g., containing one or two nitrogen atoms, said ring system optionally carrying one or more, e.g., one or two substituents, $R_6$, the substituent $R_6$ being the same as defined above for the non-fused ring substituents $R_4$.

The starting indolenine reactant may be synthesized readily by known synthetic procedures, e.g., by the intramolecular condensation of an appropriately substituted phenyl hydrazone in the presence of zinc chloride, acetic acid or alcoholic sulfuric acid, or combination of acids.

In graphic formula I, $R_5$ may be selected from the group consisting of hydrogen, methoxy, and $C_1$-$C_2$ alkyl, i.e., methyl or ethyl. Preferably, $R_5$ is hydrogen.

The organo halide with which the indolenine reactant is reacted may be represented by the formula, $R_1X$ wherein X is halogen, e.g., chloro, bromo or iodo, preferably iodo. $R_1$ is an organic group which readily undergoes addition to the nitrogen of the indolenine reactant at the temperature of the condensation reaction. While $R_1$ may be any suitable organic group, typically the selection of $R_1$ will depend upon the organo substituent desired to be added to the nitrogen atom of the indolenine, e.g., a substituent desired on the ultimate spiro(indolino)-type compound. More particularly, $R_1$ may be selected from the group consisting of $C_1$-$C_8$ alkyl, e.g., methyl, ethyl, propyl, butyl, etc., phen($C_1$-$C_4$)alkyl, e.g., benzyl, naphth($C_1$-$C_4$)alkyl, e.g., 1-naphthylmethyl, allyl, acrylyl($C_2$-$C_6$)alkyl, methacrylyl($C_2$-$C_6$)alkyl, cyano ($C_2$-$C_6$)alkyl, e.g., β-cyanoethyl, γ-cyanopropyl, β-cyanoisopropyl, and δ-cyanobutyl, $C_1$-$C_4$ acyloxy($C_2$-$C_6$)alkyl, i.e., $[R_cC(O)OR_d$, wherein $R_c$ is a $C_1$-$C_4$ alkyl and $R_d$ is a $C_2$-$C_6$ alkyl], e.g., acetoxyethyl, acetoxypropyl, propionyloxyethyl, acetoxybutyl, and propionyloxypropyl, hydroxy($C_2$-$C_6$)alkyl, e.g., hydroxyethyl, hydroxypropyl and hydroxybutyl, $(C_2H_4O)_m \bullet CH_3$, wherein m is a number of from 1 to 6. Preferably, $R_1$ is selected from the group consisting of $C_1$-$C_4$ alkyl, benzyl, 1-naphth($C_1$-$C_2$)alkyl, such as 1-naphthylmethyl, cyano($C_2$-$C_4$)alkyl, $C_1$-$C_4$ acyloxy($C_2$-$C_4$)alkyl, e.g., $C_1$-$C_4$ acyloxyethyl, hydroxy($C_2$-$C_4$)alkyl, and $(C_2H_4O)_m \bullet CH_3$, wherein m is a number of from 1 to 3, e.g., 2.

Typically, $R_1$ is selected from an alkyl group containing from 1 to 8 carbon atoms, preferably an alkyl group containing from 1 to 4 carbon atoms, in which case the reactant $R_1X$ is an alkyl halide, e.g., alkyl iodide, and the described reaction is the alkylation of an indolenine.

The condensation reaction, e.g., alkylation reaction, may be represented by the following equation.

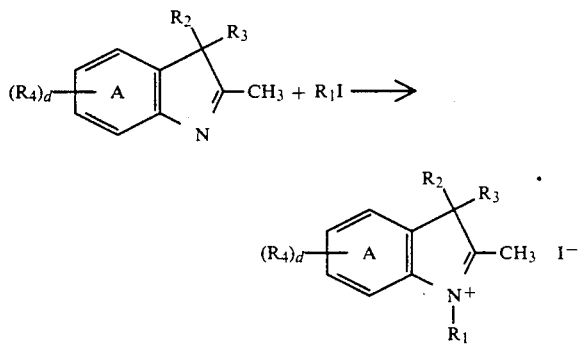

The amount of organo halide reactant ($R_1X$) used to react with the indolenine may vary from a minimum of a molar equivalent to a large molar excess. However, a large excess of organo halide reactant is not recommended for reasons of economics. Typically, the mole ratio of organo halide reactant to indolenine will range from about 1:1 to about 10:1, more typically from about 1.05:1 to about 1.2:1.

The indolenine-organo halide condensation reaction is typically carried out at temperatures of from about 75° C. to about 110° C., although lower or higher temperatures may be used. At lower temperatures, e.g., 50° C.-70° C., the reaction is relatively slow. At 70° C., condensation reactions have been found to be only 70 to 80 percent completed after 2 to 3 days at such reaction temperatures. Temperatures above about 100° C. may be used provided that such temperatures do not result in decomposition of the reactants or reaction product. The reaction temperature will depend on the boiling point of the solvent chosen (and the aforestated considerations). Temperatures above solvent reflux temperatures are not recommended. However, superatmospheric pressures are contemplated, which would permit the condensation reaction to be performed at temperatures greater than 100° C. Typically, the reaction is performed at temperatures from about 75° C. or 80° C. to about 100° C.

The present invention is more particularly described in the following examples which are intended as illustrative only as numerous modifications and variations therein will be apparent to those skilled in the art.

EXAMPLE 1

To a 500 milliliter (ml) 4-necked round bottom flask equipped with a mechanical stirrer, reflux condenser, Claisen adapter, nitrogen inlet, thermometer, Therm-o-Watch and oil bath at 50°-55° C. was added with agitation and under nitrogen, 42.5 grams (0.25 mole) of 1-iodopropane, 40.3 grams (0.20 mole) of an isomeric mixture of 2,3,4,5-tetramethyl-3-ethyl indolenine and 2,3,5,6-tetramethyl-3-ethyl indolenine, and 150 ml of 3-pentanone. (The mixture of isomers is due to the alternative directional mechanism by which intramolecular condensation occurs during formation of the indolenine reactant since indolization of 3-substituted phenyl hydrazones can give rise to a 4-substituted indole, a 6-substituted indole, or mixtures thereof. (The isomeric mixture is identified herein by placing parentheses around the numbers which identify the location of the substituent.)

The resulting yellow solution was heated to 100°–101° C. over 40 minutes and then left to stir for 22 hours. The oil bath was removed and the product solution allowed to air cool to 29°–30° C. over 1 hour. A few milligrams of seed crystals of 1-propyl-2,3,(4),5,(6)-tetramethyl-3-ethyl indoleninium iodide were added and within 10 minutes a heavy crystallization of salts was observed. The resulting slurry was stirred an additional 2 hours and left to stand over a weekend. The slurry then was cooled to about 3°–5° C. and 150 ml of diethyl ether added over 15–20 minutes. The resulting granular product was isolated on a 150 ml medium porosity sinter glass funnel and washed three times each with 50 ml of a cold diethyl ether/3-pentanone (50/50 v/v) mixture, and three times each with 50 ml of diethyl ether. The product was left under vacuum until no further liquid was observed being drawn from the filter cake, and thereafter dried. 60.3 grams of the product, 1-propyl-2,3,(4),5,(6)-tetramethyl-3-ethyl indoleninium iodide, was obtained as a light tan free-flowing salt in 81.2 percent yield.

EXAMPLE 2

The procedure of Example 1 was repeated except that 150 ml of 2-pentanone was used instead of 3-pentanone. Similar results were obtained.

EXAMPLE 3

To a 12 liter, 3-necked Morton reaction flask equipped with a mechanical stirrer, reflux condenser, nitrogen inlet and heating mantle was added with agitation at room temperature 2,3,3-trimethyl-5-methoxy indolenine (539.6 grams, 2.85 moles), 1-iodopropane (581.4 grams, 3.42 moles) and 1425 milliliters (ml) of 2-pentanone. Under nitrogen purge, the reaction mixture was heated over 38 minutes from about 32° C. to 100° C. and left to stir for about 18 hours. The reaction mixture was allowed then to air cool to about 45° C. over 1.75 hours. A few milligrams of seed crystals of 1-propyl-2,3,3-trimethyl-5-methoxy indoleninium iodide were added to the reaction mixture to initiate crystallization of the product. The resulting slurry was subsequently cooled to about 4°–6° C. and 750 ml of diethyl ether added dropwise over about 27 minutes. The crystal product was filtered and the filter cake washed with a 50/50 v/v) mixture of diethyl ether/2-pentanone (2000 ml), 2-pentanone (250 ml) and diethyl ether (250 ml). The product crystals were dried in a vacuum oven. 841.3 grams of the product, 1-propyl-2,3,3-trimethyl-5-methoxy indoleninium iodide, was obtained in 82.2 percent yield.

COMPARATIVE EXAMPLE 1

To a 300 milliliter (ml) 4-necked round bottom flask equipped with mechanical stirrer, reflux condenser, nitrogen inlet, oil bath and Therm-o-Watch was added with agitation 8.05 grams (0.04 mole) of distilled 2,3,(4),5,(6)-tetramethyl-3-ethyl indolenine and 50 ml of methylcyclohexane. This mixture was heated to about 42° C. whereupon 10.2 grams (0.06 mole) of 1-iodopropane and 24 ml methylcyclohexane were added to the reaction flask. The reaction mixture was heated with an oil bath to about 90° C. over about 30 minutes. The reaction was allowed to continue for 20 hours. After cooling to room temperature, the methylcyclohexane solvent was decanted. The product remained in the reaction flask as a light yellow-brown viscous syrup. A workup of the product, i.e., 1-propyl-2,3,(4),5,(6)-tetramethyl-3-ethyl indoleninium iodide resulted in an isolated yield of only 12.8 percent.

COMPARATIVE EXAMPLE 2

Into a 250 milliliter (ml) 3-neck round bottom flask equipped with mechanical stirrer, reflux condenser, nitrogen inlet, thermometer and oil bath was charged 8.05 grams (0.04 mole) of the indolenine of Comparative Example 1 and 50 ml of propyl propionate. Thereupon, 10.2 grams (0.06 mole) of 1-iodopropane and 24 ml of propyl propionate were charged to the reaction flask. The reaction mixture was heated over about 40 minutes to about 86° C. and maintained at that temperature for about 48 hours. After cooling, the product, a tarry salt, was observed to have stuck to the walls of the reactor. The product, 1-propyl-2,3,(4),5,(6)-tetramethyl-3-ethyl indoleninium iodide was recovered in about 32.3 percent yield.

COMPARATIVE EXAMPLE 3

In accordance with the procedure of Comparative Example 1, 16.5 grams (0.082 mole) of the indolenine of Comparative Example 1 and 50 milliliters (ml) of tertiary amyl alcohol were charged to the reaction flask. To this solution were added 21.3 grams of 1-iodopropane and 100 ml of tertiary amyl alcohol. The reaction mixture was heated to about 97°–99° C. and reacted for 22 hours. The reaction mixture remained liquid. A small amount of product seed crystals was added to the reaction mixture which was then cooled to about 5° C. On standing over a weekend, a coating of the product, 1-propyl-2,3,(4),5,(6)-tetramethyl-3-ethyl indoleninium iodide, deposited on the inside walls of the reaction flask. The product was easily removed but was obtained in only 37.7 percent yield.

The results of Examples 1–3 and Comparative Examples 1–3 show that indoleninium iodides can be readily prepared in high yields as relatively pure salts by reaction of a corresponding indolenine with an organic halide reactant in the presence of a relatively high-boiling organic ketone. When solvents such as methylcyclohexane, propyl propionate or t-amyl alcohol are used, the product is obtained in relatively low yields and, except for the alcohol, is obtained in a physical form, i.e., a very viscous syrup to tarry solidified mass, that is difficult to purify.

Although the present invention has been described with reference to the specific details of particular embodiments, it is not intended that such details be regarded as limitations upon the scope of the invention except as and to the extent that they are included in the accompanying claims.

What is claimed is:

1. In the process of preparing an indoleninium halide by reaction of the corresponding indolenine with an organo halide reactant, the organo portion of which undergoes addition to the nitrogen of the indolenine, the improvement wherein the reaction is conducted in the presence of a solvating amount of organic ketone solvent which boils between about 80° C. and about 200° C..

2. The process of claim 1 wherein the organic ketone solvent is selected from the group consisting of acyclic ketones containing from 4 to 12 carbon atoms and alicyclic ketones containing from 4 to 10 carbon atoms.

3. The process of claim 2 wherein the organic ketone solvent is selected from the group consisting of acyclic ketones containing from 4 to 8 carbon atoms, and alicyclic ketones containing from 5 to 7 carbon atoms.

4. The process of claim 1 wherein the organic ketone solvent is selected from the group consisting of butanone, 3-methyl-2-butanone, 2-pentanone, 3-pentanone, 4-methyl-2-pentanone, 3-hexanone, 2-hexanone, 5-methyl-2-hexanone, 2-heptanone, 3-heptanone, 4-heptanone, 5-methyl-3-heptanone, 2-octanone, 3-octanone, cyclopentanone, cyclohexanone, 2-methylcyclohexanone and cycloheptanone.

5. The process of claim 3 wherein the organic ketone solvent is selected from the group consisting of butanone, 3-methyl-2-butanone, 2-pentanone, 3-pentanone, 4-methyl-2-pentanone, 5-methyl-2-hexanone, 2-methyl-3-heptanone, 5-methyl-3-heptanone, cyclopentanone, cyclohexanone and 2-methylcyclohexanone.

6. The process of claim 1 wherein the organic ketone solvent boils between about 80° C. and about 130° C.

7. The process of claim 1 wherein the amount of organic ketone solvent used is from about 1 to about 5 milliliters of solvent per gram of indoleninium halide product.

8. The process of claim 7 wherein the amount of organic ketone solvent used is from about 2 to about 3 milliliters of solvent per gram of indoleninium halide product.

9. The process of claim 1 wherein the indolenine is represented by the graphic formula,

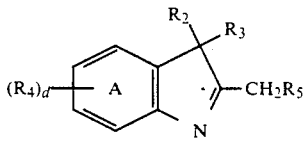

wherein:
(a) $R_2$ and $R_3$ are each selected from the group consisting of $C_1$-$C_5$ alkyl, phenyl, mono- and di-substituted phenyl, benzyl, or $R_2$ and $R_3$ combine to form a cyclic ring selected from the group consisting of an alicyclic ring cnotaining from 5 to 8 carbon atoms (including the spiro carbon atom), the phenyl substituents being selected from the group consisting of $C_1$-$C_4$ alkyl and $C_1$-$C_4$ alkoxy,
(b) $R_5$ is selected from the group consisting of hydrogen methoxy and $C_1$-$C_2$ alkyl,
(c) each $R_4$ is selected (i) from the group consisting of $C_1$-$C_5$ alkyl, halogen, $C_1$-$C_5$ alkoxy, nitro, cyano, $C_1$-$C_4$ monohaloalkyl, $C_1$-$C_4$ polyhaloalkyl, $C_1$-$C_8$ alkoxycarbonyl, and $C_1$-$C_4$ acyloxy, or (ii) $(R_4)_d$ is a ring system fused to the ring A, which ring system comprises an aromatic or heteroaromatic ring and optionally having one or more substituents, $R_6$, said $R_6$ substituent being the same as defined for $R_4$, and
(d) the letter "d" is an integer from 0 to 4.

10. The process of claim 1 wherein the organo halide reactant is represented by the formula, $R_1X$, wherein X is chloro, bromo, or iodo and $R_1$ is selected from the group consisting of $C_1$-$C_8$ alkyl, phen($C_1$-$C_4$)alkyl, naphth($C_1$-$C_4$)alkyl, allyl, acrylyl ($C_2$-$C_6$)alkyl, methacrylyl($C_2$-$C_6$)alkyl, cyano($C_2$-$C_6$)alkyl, $C_1$-$C_4$ acyloxy($C_2$-$C_6$)alkyl, hydroxy($C_2$-$C_6$)alkyl, and $(C_2H_4O)_m \cdot CH_3$, wherein m is a number of from 1 to 6.

11. The process of claim 1 wherein the mole ratio of organo halide to indolenine varies from about 1:1 to about 10:1.

12. The process of claim 11 wherein the mole ratio of organo halide to indolenine varies from about 1.05:1 to about 1.2:1.

13. In the process of preparing an indoleninium halide by reaction of the corresponding indolenine with an organo halide reactant, the organo portion of which undergoes addition to the nitrogen of the indolenine, the improvement wherein the reaction is conducted in the presence of a solvating amount of an organic ketone solvent which boils between about 80° C. and about 130° C., said indolenine being represented by the graphic formula,

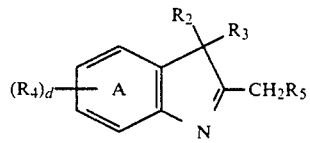

wherein:
(a) $R_2$ and $R_3$ are each selected from the group consisting of $C_1$-$C_5$ alkyl and phenyl,
(b) $R_5$ is hydrogen,
(c) each $R_4$ is selected from the group consisting of $C_1$-$C_5$ alkyl, halogen, $C_1$-$C_5$ alkoxy, nitro, cyano, $C_1$-$C_4$ monohaloalkyl, $C_1$-$C_4$ Polyhaloalkyl, $C_1$-$C_8$ alkoxycarbonyl, and $C_1$-$C_4$ acyloxy, and
(d) the letter "d" is an integer of from 0 to 2, and said organo halide is represented by the formula $R_1X$, wherein X is chloro, bromo or iodo and $R_1$ is selected from the group consisting of $C_1$-$C_8$ alkyl, phen($C_1$-$C_4$)alkyl, naphth($C_1$-$C_4$)alkyl, allyl, acrylyl ($C_2$-$C_6$)alkyl, methacrylyl($C_2$-$C_6$)alkyl, cyano($C_2$-$C_6$)alkyl, $C_1$-$C_4$ acyloxy($C_2$-$C_6$)alkyl, hydroxy($C_2$-$C_6$)alkyl, and $(C_2H_4O)_m \cdot CH_3$, wherein m is a number of from 1 to 6.

14. The process of claim 13 wherein the organic ketone solvent is selected from the group consisting of acyclic ketones containing from 4 to 8 carbon atoms, and alicyclic ketones containing from 5 to 7 carbon atoms.

15. The process of claim 14 wherein the organic ketone solvent is selected from the group consisting of butanone, 3-methyl-2-butanone, 2-pentanone, 3-pentanone, 4-methyl-2-pentanone, 5-methyl-2-hexanone, 2-methyl-3-heptanone, 5-methyl-3-heptanone, cyclopentanone, cyclohexanone and 2-methylcyclohexanone.

16. The process of claim 13 wherein the amount of organic ketone solvent used is from about 1 to about 5 milliliters of solvent per gram of indoleninium halide product.

17. The process of claim 16 wherein the mole ratio of organo halide to indolenine varies from about 1:1 to about 10:1.

18. The process of claim 17 wherein $R_1$ is $C_1$-$C_8$ alkyl and X is iodo.

* * * * *